United States Patent [19]

Ishikawa

[11] Patent Number: 5,072,108
[45] Date of Patent: Dec. 10, 1991

[54] FOREIGN OBJECT DETECTING METHOD AND DEVICE

[75] Inventor: Kazushi Ishikawa, Yokohama, Japan

[73] Assignee: Kabushiki Kaisha Kirin Techno System, Yokohama, Japan

[21] Appl. No.: 578,190

[22] Filed: Sep. 6, 1990

[30] Foreign Application Priority Data

Sep. 8, 1989 [JP] Japan ................................ 1-234174

[51] Int. Cl.⁵ ............................................. G01N 9/04
[52] U.S. Cl. .................................. 250/223 B; 356/427
[58] Field of Search ....................... 250/223 B, 233 R; 356/427, 428, 240

[56] References Cited

U.S. PATENT DOCUMENTS

| | | | |
|---|---|---|---|
| 3,528,544 | 9/1970 | Noguchi et al. | 356/427 |
| 3,811,567 | 5/1974 | Tomita et al. | 356/427 |
| 4,095,904 | 6/1978 | Klein et al. | 356/427 |
| 4,241,256 | 12/1980 | Tagaya et al. | 250/223 B |
| 4,636,635 | 1/1987 | Krönseder | 250/223 B |
| 4,680,463 | 7/1987 | Lutgendorf et al. | 250/223 B |

Primary Examiner—David C. Nelms
Assistant Examiner—Que T. Le
Attorney, Agent, or Firm—Fleit, Jacobson, Cohn, Price, Holman & Stern

[57] ABSTRACT

A foreign object detecting method and device are for detecting foreign objects mixed in a liquid filling a transparent container. The foreign object detecting method comprises the first step of keeping for a set period of time the transparent container rotated in a first rotational direction, the second step of rotating the transparent container in a second rotational direction opposite to the first rotational direction; the third step of taking a transmitted light image of the transparent container while the liquid in the transparent container is substantially stopped after a set period of time from the start of the rotation of the transparent container in the second rotational direction; and the fourth step of scanning the taken transmitted light image along the rotational directions to detect the foreign objects in the liquid based on a difference in brightness between at least two points on a scanning line. Thus the foreign objects mixed in the liquid can be detected discriminately from the flaws and smears of the transparent bottle per se.

18 Claims, 4 Drawing Sheets

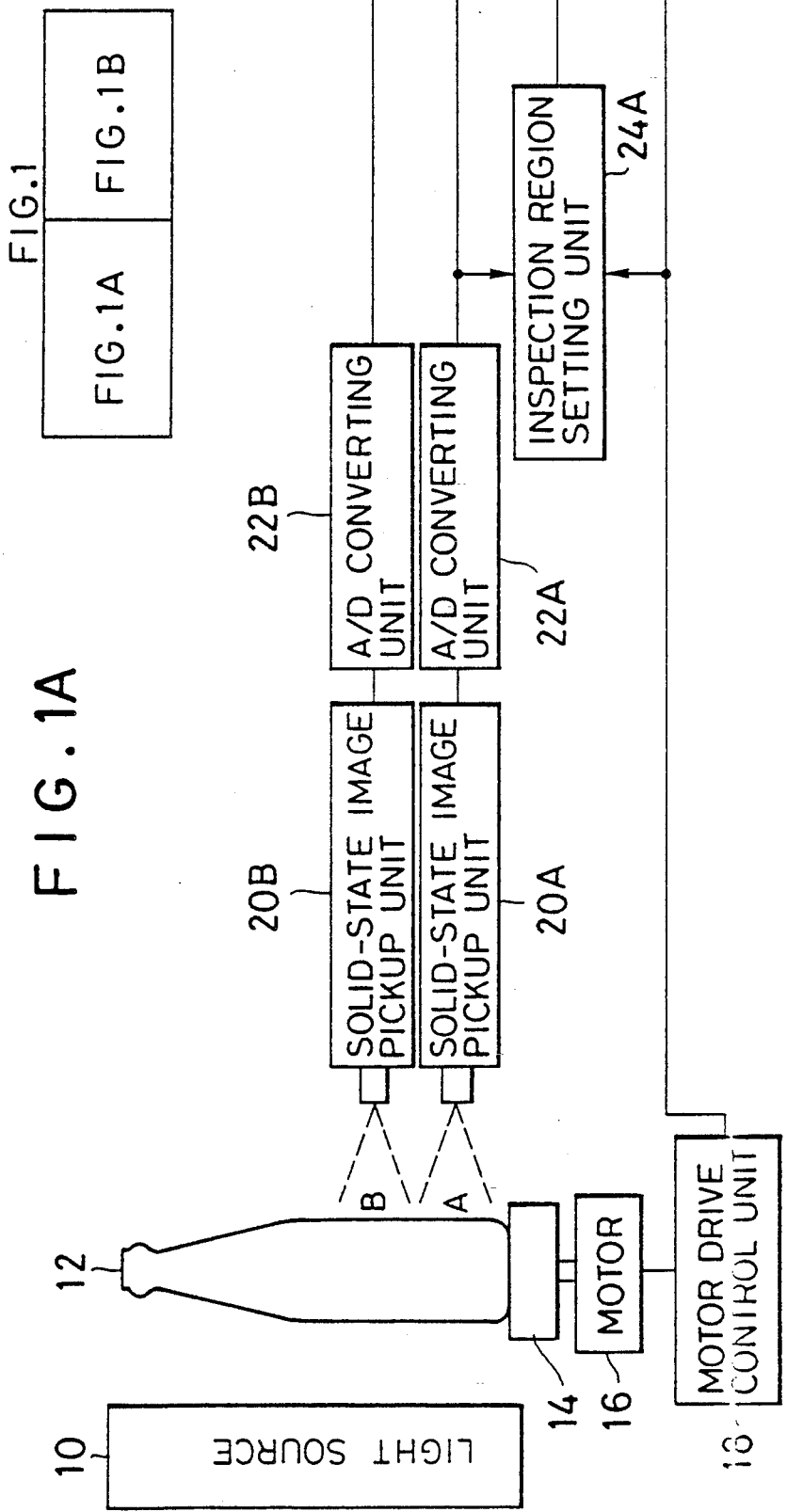

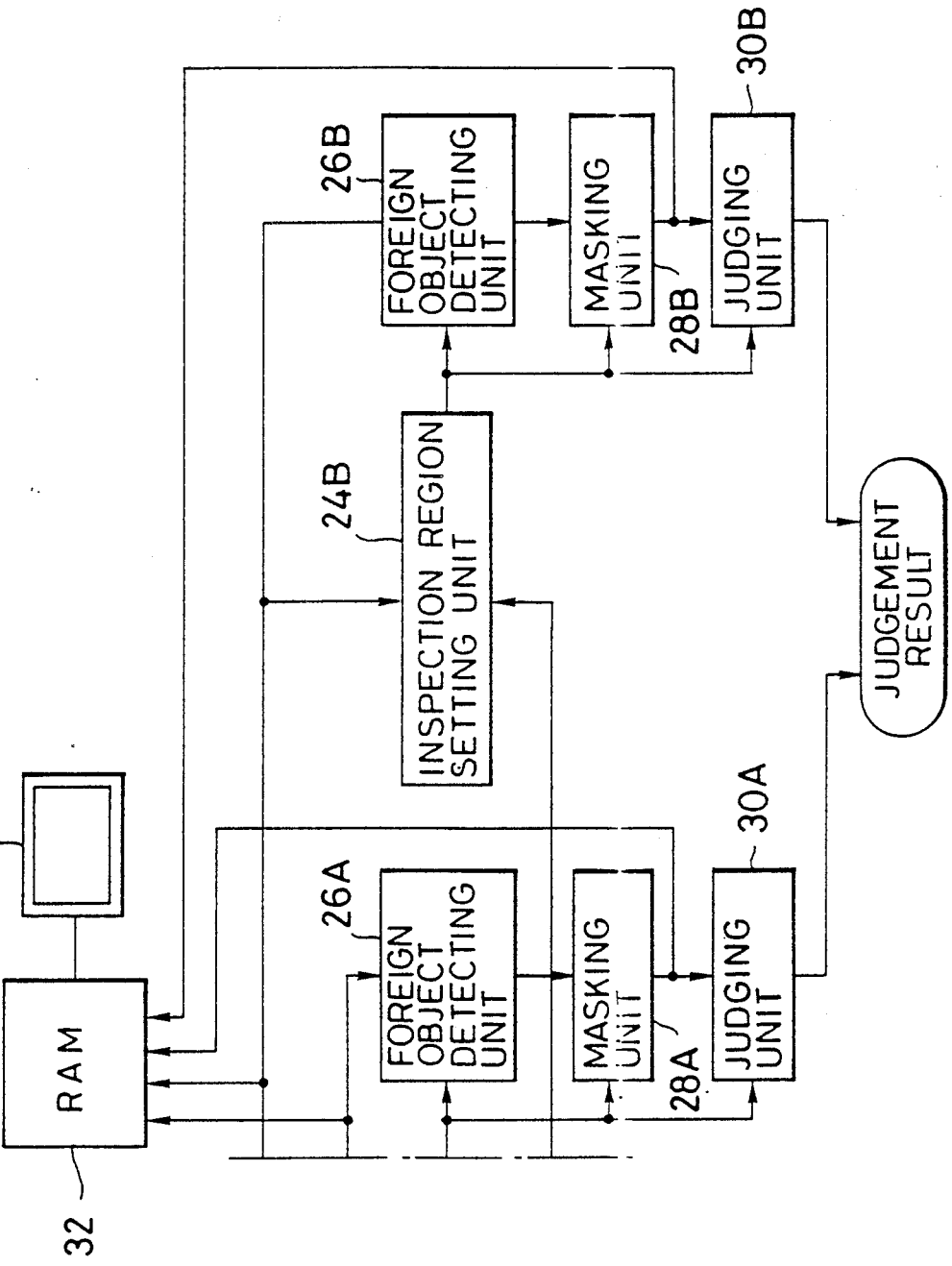

FOREIGN OBJECT DETECTING METHOD AND DEVICE

BACKGROUND OF THE INVENTION

This invention relates to a method and a device for detecting foreign objects mixed in a liquid filling a transparent container.

It is necessary that the beer bottles filled with beer are detected as to whether foreign objects are mixed in the beer before their delivery. The foreign objects mixed in the beer are fungi, biomasses, fractions of rust, fractions of labels, etc. and have various sizes. Some of the foreign objects are as small as around 1 mm$\phi$, and others are as large as 10 mm$\phi$. The foreign object detection for detecting such foregin objects with accuracy has been conducted visually by detectors, and the labor savings have been expected.

As a device for detecting defects of a bottle and foreign objects attached to the bottle has been known a bottle inspecting device in which a transmitted light image of a bottle is taken by a CCD camera, and, based on the transmitted light image, defects and foreign objects are detected. But the conventional bottle inspecting device is for detecting defects of an foreign objects in a bottle having few flaws on the outer surface, and has found it difficult to discriminate foreign objects mixed in a liquid in the bottle, such as a beer bottle, with a number of defects on the outer surface from the defects.

Thus conventionally it has been impossible to detect with high accuracy foreign objects in a liquid filling a transparent bottle with a comparatively large number of flaws on the outer surface.

SUMMARY OF THE INVENTION

An object of this invention is to provide a foreign object detecting method and a device for detecting with accuracy the foreign objects mixed in a liquid filling a transparent container.

This object is achieved by a foreign object detecting method for detecting foreign objects mixed in a liquid filling a transparent container, comprising: the first step of keeping for a set period of time the transparent container rotated in a first rotational direction; the second step of rotating the transparent container in a second rotational direction opposite to the first rotational direction; the third step of taking a transmitted light image of the transparent container while the liquid in the transparent container is substantially stopped after a set period of time from the start of the rotation of the transparent container in the second rotational direction; and the fourth step of scanning the taken transmitted light image along the rotational directions to detect the foreign objects in the liquid based on a difference in brightness between at least two points on a scanning line.

This object is achieved by a foreign object detecting device for detecting foreign objects mixed in a liquid filling a transparent container, comprising: a motor unit for rotating the transparent container, a motor drive control unit for controlling the drive of the motor unit so as to keep the transparent container rotated in a first rotational direction for a set period of time, and subsequently to rotate the transparent container in a second rotational direction opposite to the first rotational direction for the detection of the foreign objects; an image pickup unit for taking a transmitted light image of the transparent container while the liquid in the transparent container is substantially stopped after a set period of time from the start of the rotation of the transparent container in the second rotational direction; and a foreign object detecting unit for scanning the taken transmitted light image along the rotational directions, and detecting the foreign objects in the liquid based on a difference in brightness between at least two points on a scanning line.

According to this invention, after a transparent bottle is kept still or rotated in a first rotational direction for a set period of time, the bottle is rotated in a second rotational direction opposite to the first rotational direction, and after a set period of time from the start of the rotation of the bottle in the second rotational direction, a transmitted light image of the transparent bottle is taken while a liquid in the transparent bottle is substantially still, and the taken transmitted light image is scanned along the rotational directions of the transparent bottle, whereby the foreign objects mixed in the liquid can be detected discriminately from the flaws and smears of the transparent bottle per se. Thus the foreign objects mixed in the liquid filling a transparent bottle with flaws on the outer surface can be detected with accuracy.

BRIEF DESCRIPTION OF THE DRAWINGS

FIGS. 1a and 1b are a block diagram of the foreign object detecting device according to one embodiment of this invention; and;

DETAILED DESCRIPTION OF THE INVENTION

Figure 2:
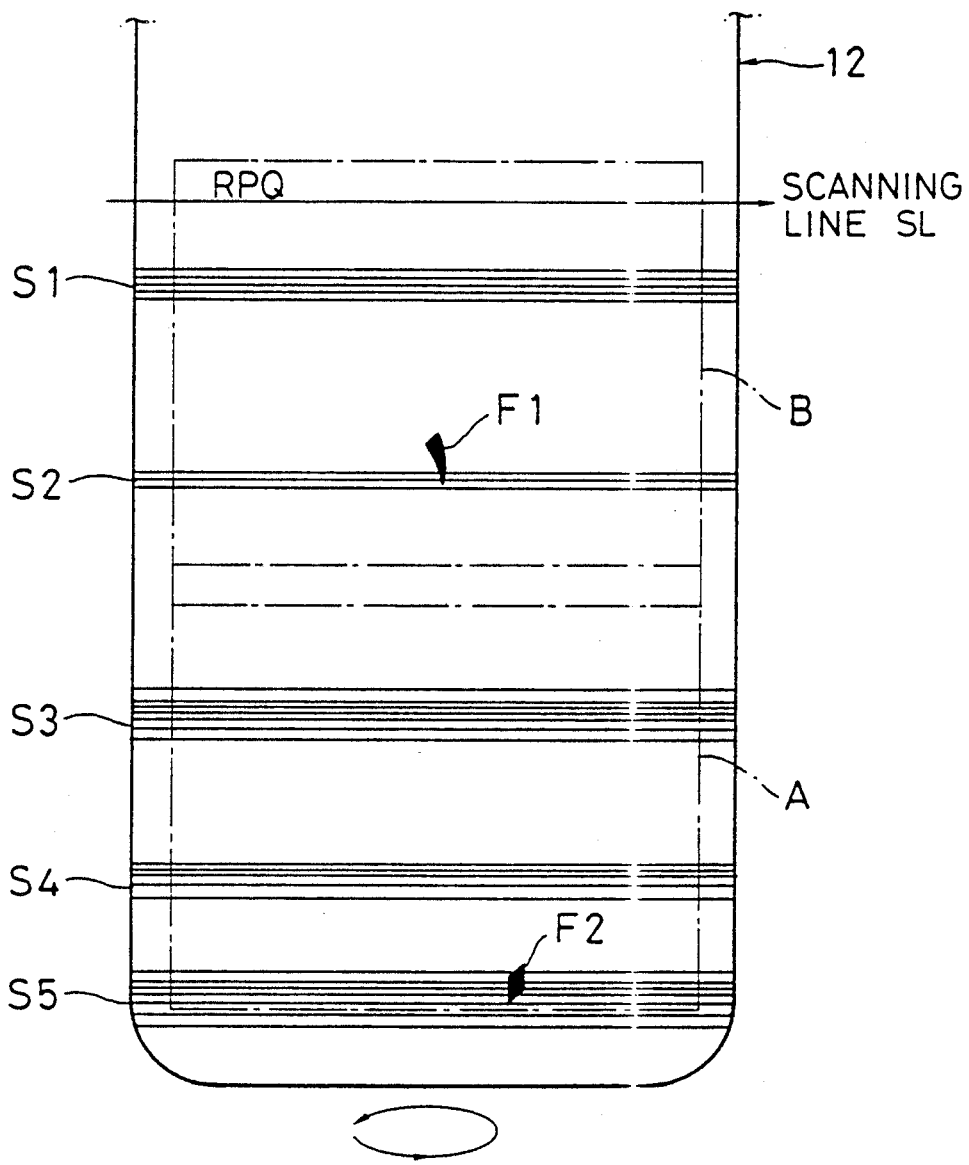
FIGS. 2 and 3 are views of images taken on the screen of the foreign object detecting device of FIG. 1.

The foreign object detecting device according to one embodiment of this invention will be explained with reference to FIGS. 1a, 1b, 2 and 3. This embodiment will be explained by means of a beer bottle filled with beer.

A light source 10 is disposed behind a beer bottle 12 to irradiate the bottle to be inspected. Beer bottles 12 to be inspected are carried on a conveyor (not shown) to be mounted one by one on a rotary table 14. The rotary table 14 is rotated by a motor 16, and the drive of the motor 16 is controlled by a motor drive control unit 18. A characteristic of this invention lies in the drive control of the motor 16 by the motor drive control unit 18.

Usually some beer bottles 12 have a considerable number of flaws on the outer surfaces, and some foreign objects to be inspected are smaller than the flaws. Thus it is difficult to discriminate the foreign objects from the flaws on the outer surfaces by taking an image of a beer bottle 12 at a standstill. In this embodiment, the rotation of a beer bottle 12 is controlled so that the flaws on the outer surface of the beer bottle 12 are blurred to thereby keep only the beer in the bottle 12 still. That is, when the beer bottle 12 is rotated, as shown in FIG. 2, flaws S1 to S5 are blurred horizontally, but the beer in the bottle 12 is still, and foreign objects F1, F2 can be discriminated from the flaws S1 to S5.

To this end, the motor drive control unit 18 performs the following control. First, the beer bottle to be inspected 12 is kept rotated in the first rotational direction with the beer in the bottle 12 rotated in the same first rotational direction. Then, the beer bottle 12 is abruptly stopped, and after a set period of time, the beer bottle 12 is abruptly rotated in the second rotational direction opposite to the first rotational direction. At this time, the beer bottle 12 per se rotates in the second rotational direction, but the beer in the bottle 12, due to inertia, stops with a delay and then gradually begins to rotate in the second rotational direction. In this embodiment, an inspection is conducted at a timing of the stop of the beer in the bottle 12 to be inspected. The motor drive control unit 18 outputs a timing signal indicative of the above-described timing for the inspection of the beer bottle 12.

The beer bottle 12 to be inspected is rotated in the first rotational direction so as to rotate in the beer the suspending or deposited foreign objects. The rotation speed in the first rotational direction may be higher than a minimum rotation speed which can rotate in the beer the foreign objects in the beer bottle 12. In this embodiment, the rotation speed was around 440 rpm.

Then the beer bottle 12 is abruptly stopped and is kept still for a set period of time before the bottle 12 is rotated in the second rotational direction so as to collect the foreign objects on rotation at the center of the beer bottle to facilitate their detection. The set stopping period of time may be more than a minimum stopping period of time in which the foreign objects gather at the center of the beer bottle 12. In this embodiment, the minimum stopping period of time following the rotation at around 440 rpm was around 0.6 seconds. As the rotation speed for the rotation in the first rotational direction increases, the above-described minimum stopping period of time becomes longer.

The beer bottle 12 is rotated in the second rotational direction in an inspection is for blurring the flaws on the outer surface of the beer bottle 12. The rotation speed in the second rotational direction is a minimum rotation speed which the flaws on the outer surface of the beer bottle so much blur along the rotational direction in one frame that the detection of the flaws becomes difficult. In this embodiment the minimum rotation speed was around 700 rpm.

One example of the timing for the inspection of the beer bottle 12 will be explained below. In this example, the beer bottle 12 is rotated in the first rotational direction for around 1 second at around 440 rpm. Then the beer bottle 12 is abruptly stopped, and after around 0.6 seconds. The beer bottle 12 is rotated in the second rotational direction at around 720 rpm. After around 0.6 seconds from the abrupt stop, the beer bottle 12 is rotated in the second rotational direction. After around 0.6 seconds from the start of the rotation in the second rotational direction, 7 frames are taken as an image for the detection of the foreign objects, and the objects are detected. One frame is 16.6 msec, and in this example, the inspection period of time is 116.2 msec. The inspection can be conducted at 380 BPM (bottle per minute).

Another example of the timing of the inspection of the beer bottle 12 will be explained. First, the beer bottle 12 is kept still with the beer being also still. Then the bottle 12 is abruptly rotated in one direction at 700 rpm. Seven frames are taken around 0.2 seconds after the start of the rotation and prior to the start of the beer in the bottle 12, and the foreign objects are detected. This example has an advantage that the drive control is easier than the first example.

A transmitted light image of the beer bottle 12 is taken by two solid-state image pickup devices 20A, 20B. Some foreign objects mixed in the beer of the beer bottle 12 are as small as 1 mm$\phi$, and these small foreign objects have to be taken a transmitted light image of with high resolution. The solid-state image pickup device 20A lower positioned is for detecting the foreign objects deposited on the bottom of the beer bottle 12. The solid-state image pickup device 20B higher positioned is for detecting the foreign objects suspended in the beer.

Analog image signals outputted by the solidstate image pickup devices 20A, 20B are A/D-converted into digital image signals respectively by A/D converting units 22A, 22B. The A/D converted digital image signals are outputted to respective inspection region setting units 24A, 24B and to respective foreign object detecting units 26A, 26B.

The inspection region setting units 24A, 24B select frames of the taken transmitted light image to be inspected, based on a timing signal from the motor drive control unit 18, and set inspection regions A, B as indicated by the one-dot chain line in FIG. 2, based on the transmitted light image of the beer bottle 12 in the selected frames. The inspection regions A, B overlap each other on their borders.

The method for setting the right and the left edges of the inspection regions A, B will be explained below.

Since the right and the left edges of the image of the beer bottle 12 are darker, based on the image of the beer bottle 12, the right and the left edges of the image are detected, and the right and the left edges of the inspection regions A, B are set at positions which are inward from the edges of the image by a set distance.

The method for setting the upper and the lower edges of the inspection region A will be explained with reference to FIG. 3.

Figure 3:
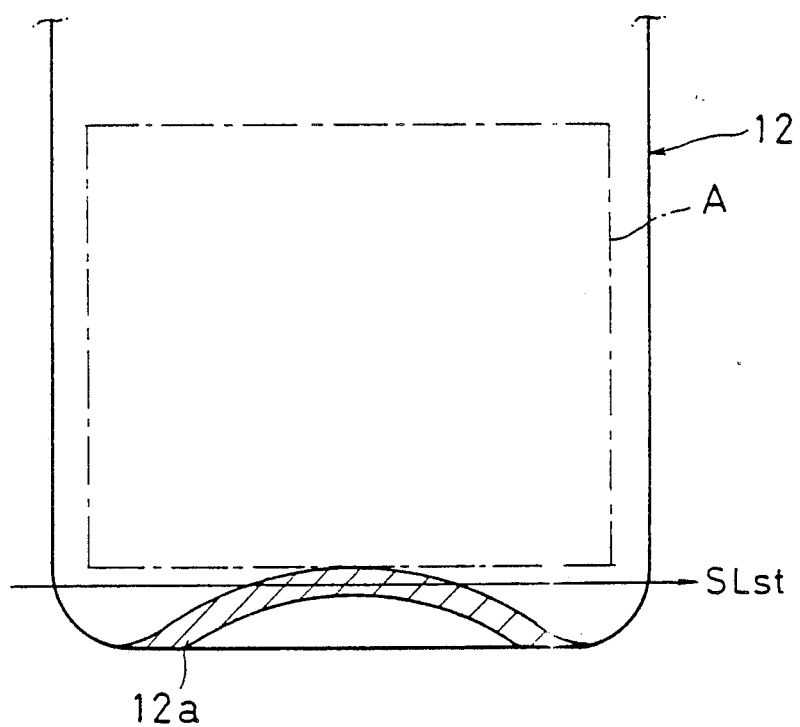

As shown in FIG. 3, the bottle bottom 12a of the image of the beer bottle 12 appears in a darker circular arc stripe curving upward at the center. The image is scanned by the horizontal scanning line sequentially from the upper to count picture elements which are darker than a set threshold value for the detection of the bottle bottom 12 of the image. The scanning line on which darker picture elements of the bottle bottom 12a reach the set threshold value is taken as the standard scanning line SLst of the bottle bottom. With the scanning line SLst set as the standard, the lower edge of the inspection region A is set.

It is preferable to set a position slightly overlapping the upper edge of the bottle bottom 12a as the lower edge of the inspection region A. This is because heavy foreign objects which are deposited in the beer bottle 12 tend to gather immediately above the bottle bottom 12a.

The edges of the image of the beer bottle 12 are thus detected to set the inspection regions A, B, which enables the inspection regions A, B to be set in accordance with a movement of the beer bottle 12. The inspection region setting units 26A, 26B output inspection gate signals to foreign object detecting units 26A, 26B, to masking units 28A, 28B and to judging units 30A, 30B. When the outer edge of the beer bottle 12 is obscure, the inspection region setting units 24A, 24B may fix the inspection regions A, B.

The foreign object detecting units 26A, 26B detect foreign objects, based on the digital image signals from the A/D converting units 22A, 22B. As shown in FIG. 2, for prohibiting the detection of the horizontally blurred images of the flaws S1 to S5, the foreign object detecting units 26A, 26B detect the foreign objects along a horizontal scanning line SL along the rotational direction of the beer bottle 12. That is, at least two points along the scanning line SL are compared with each other in brightness for the detection of the foreign objects.

In the two-point detecting method, for example, a point to be inspected P and a point Q spaced from the point P by a set distance are compared in brightness, and based on a brightness difference, it is detected whether or not the point P is a foreign object detected point. In the three-point detecting method, a point to be inspected P, and neighboring points Q, R spaced from the point P by a set distance are compared in brightness, and based on a brightness difference, it is detected whether or not the point P is a foreign object detected point. Other various methods may be used as required.

Foreign object detection signals from the foreign object detecting units 26A, 26B are masked by the masking units 28A, 28B. When the foreign object detecting units 26A, 26B increase the sensitivity for the prevention of erroneous detections, sometimes parts which are not foreign objects are erroneously detected as foreign object detected points. The masking is for removing such erroneous foreign object detected points. There are various masking methods, but the continuous masking method is used in this embodiment.

An actual foreign object is indicated by continuous foreign object detection signals in accordance with the size. Parts which are not foreign objects are indicated by scattered foreign detection signals. The masking processing removes as false foreign objects the isolated foreign object detection signal and the foreign object detection signals which are continuous only below a set value.

The judging units 30A, 30B judge the presence of an foreign object, based on a foreign object detection signal supplied by the masking unit 28A, 28B. The judging units 30A, 30B judge that the beer bottle contains a foreign object, for example, when a total number of foreign object detected points exceeds a set value. In this embodiment, when it is judged that either of the inspection regions A, B contains a foreign object, a judgement signal is supplied to a conveying system (not shown) of the beer bottle 12. Then the conveying system expels the beer bottle, based on the judgement signal.

A RAM 32 and a monitor 34 are provided for monitoring the transmitted light image. The RAM 32 is supplied with the digital image signal which has been A/D-converted by the A/D converting units 22A, 22B, and the foreign object detection signal masked by the masking units 28A, 28B.

Thus, this embodiment can detect with accuracy the foreign objects in the beer filling a beer bottle. The beer bottles expelled by the foreign object detecting device according to this embodiment were visually inspected as done conventionally, and it was found that the foreign object detecting device according to this embodiment expelled with accuracy the bottles containing foreign objects.

This invention is not limited to the above-described embodiments and covers various modifications.

Although the above-described embodiments have detected foreign objects in beer bottles, this invention is applicable to the detection of foreign objects in the liquids filling transparent containers other than beer bottles.

What is claimed is:

1. A foreign object detecting method for detecting foreign objects mixed in a liquid filling a transparent container, comprising:

a first step of keeping for a set period of time the transparent container rotated in a first rotational direction;

a second step of rotating the transparent container in a second rotational direction opposite to the first rotational direction;

a third step of taking a transmitted light image of the transparent container while the liquid in the transparent container is substantially stopped after a set period of time from the start of the rotation of the transparent container in the second rotational direction; and a fourth step of scanning the taken transmitted light image along the rotational directions to detect the foreign objects in the liquid based on a difference in brightness between at least two points on a scanning line.

2. A foreign object detecting method according to claim 1, further comprising a step of stopping the transparent container for a set period of time so as to gather the foreign objects at the center of the transparent container, the step following the first step before the second step.

3. A foreign object detecting method according to claim 1, further comprising the step of detecting a position of the bottom of the transparent container based on the transmitted light image of the transparent container, and setting an inspection region with the position of the bottom set as a standard position, the step following the third step before the fourth step.

4. A foreign object detecting method for detecting foreign objects in a liquid filling a transparent container, comprising:

a first step of keeping the transparent container still for a set period of time;

a second step of rotating the transparent container in one rotational direction;

a third step of taking a transmitted light image of the transparent container while the flaws on the outer surface of the transparent container are blurred after set period of time from the start of the rotation of the transparent container in the one rotational direction; and a fourth step of scanning the taken transmitted light image along the rotational direction to detect the foreign objects in the liquid based on a difference in brightness between at least two points on a scanning line.

5. A foreign object detecting method according to claim 2, further comprising the step of detecting a position of the bottom of the transparent container based on the transmitted light image of the transparent container, and setting an inspection region with the position of the bottom set as a standard position, the step following the third step before the fourth step.

6. A foreign object detecting method according to claim 4, further comprising the step of detecting a position of the bottom of the transparent container based on the transmitted light image of the transparent container, and setting an inspection region with the position of the bottom set as a standard position, the step following the third step before the fourth step.

7. A foreign object detecting device for detecting foreign objects mixed in a liquid filling a transparent container, comprising:

a motor unit for rotating the transparent container, a motor drive control unit for controlling the drive of the motor unit so as to keep the transparent container rotated in a first rotational direction for a set period of time, and subsequently to rotate the transparent container in a second rotational direction opposite to the first rotational direction for the detection of the foreign objects;

an image pickup unit for taking a transmitted light image of the transparent container while the liquid in the transparent container is substantially stopped after a set period of time from the start of the rotation of the transparent container in the second rotational direction; and a foreign object detecting unit for scanning the taken transmitted light image along the rotational directions, and detecting the foreign objects in the liquid based on a difference in brightness between at least two points on a scanning line.

8. A foreign object detecting device according to claim 7, wherein the motor drive control unit keeps the transparent container still for a set period of time so as to gather the foreign objects at the center of the transparent container before the transparent container is rotated in the second rotational direction.

9. A foreign object detecting device according to claim 7, further comprising an inspection region setting unit for detecting a position of the bottom of the transparent container based on the transmitted light image of the transparent container, and setting an inspection region with the position of the bottom set as a standard position.

10. A foreign object detecting device according to claim 8, further comprising an inspection region setting unit for detecting a position of the bottom of the transparent container based on the transmitted light image of the transparent container, and setting an inspection region with the position of the bottom set as a standard position.

11. A foreign object detecting device according to claim 7, wherein the foreign objects detecting unit comprising:

foreign object detecting means for comparing at least two point on a scanning line in brightness, and recognizing a foreign object detected point when the difference in brightness exceeds a set value; and judging means for judging the presence of the foreign objects based on a number of the foreign object detected points recognized by the foreign object detecting means.

12. A foreign object detecting device according to claim 8, wherein the foreign objects detecting unit comprising:

foreign object detecting means for comparing at least two point on a scanning line in brightness, and recognizing a foreign object detected point when the difference in brightness exceeds a set value; and judging means for judging the presence of the foreign objects based on a number of the foreign object detected points recognized by the foreign objects detecting means.

13. A foreign object detecting device according to claim 9, wherein the foreign objects detecting unit comprising:

foreign object detecting means for comparing at least two point on a scanning line in brightness, and recognizing a foreign object detected point when the difference in brightness exceeds a set value; and judging means for judging the presence of the foreign objects based on a number of the foreign object detected points recognized by the foreign object detecting means.

14. A foreign object detecting device according to claim 10, wherein the foreign objects detecting unit comprising:

foreign object detecting means for comparing at least two point on a scanning line in brightness, and recognizing a foreign object detected point when the difference in brightness exceeds a set value; and judging means for judging the presence of the foreign objects based on a number of the foreign object detected points recognized by the foreign object detecting means.

15. A foreign object detecting device for detecting foreign objects mixed in a liquid filling a transparent container, comprising:

a motor unit for rotating the transparent container;

a motor drive control unit for controlling the drive of the motor unit so as to keep the transparent container still for a set period of time, and subsequently to rotate the transparent container in one rotational direction for the detection of the foreign objects;

an image pickup unit for taking a transmitted light image of the transparent container while the flaws on the outer surface of the transparent container are blurred after a set period of time from the start of the rotation of the transparent container in the one rotational direction; and;

a foreign object detecting unit for scanning the taken transmitted light image along the rotational direction, and detecting the foreign objects in the liquid based on a difference in brightness between at least two points on a scanning line.

16. A foreign object detecting device according to claim 15, further comprising an inspection region setting unit for detecting a position of the bottom of the transparent container based on the transmitted light image of the transparent container, and setting an inspection region with the position of the bottom set as a standard position.

17. A foreign object detecting device according to claim 15, wherein the foreign objects detecting unit comprising:

foreign object detecting means for comparing at least two point on a scanning line in brightness, and recognizing a foreign object detected point when the difference in brightness exceeds a set value; and judging means for judging the presence of the foreign objects based on a number of the foreign object detected points recognized by the foreign object detecting means.

18. A foreign object detecting device according to claim 16, wherein the foreign objects detecting unit comprising:

foreign object detecting means for comparing at least two point on a scanning line in brightness, and recognizing a foreign object detected point when the difference in brightness exceeds a set value; and judging means for judging the presence of the foreign objects based on a number of the foreign object detected points recognized by the foreign object detecting means.

* * * * *